United States Patent
Wu et al.

(10) Patent No.: US 6,593,503 B1
(45) Date of Patent: *Jul. 15, 2003

(54) PROCESS FOR MAKING AROMATIC HYDROCARBONS USING AN ACID TREATED ZEOLITE

(75) Inventors: An-hsiang Wu, Bartlesville; Charles A. Drake, Nowata; Ralph J. Melton, Bartlesville, all of OK (US)

(73) Assignee: Phillips Petroleum Company, Bartlesville, OK (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/695,482

(22) Filed: Aug. 12, 1996

(51) Int. Cl.$^7$ .................................................. C07C 6/00
(52) U.S. Cl. ........................ 585/419; 585/418; 585/488; 585/489; 208/136; 208/137; 208/138
(58) Field of Search ................................ 208/136, 137, 208/138; 585/418, 419, 488, 489

(56) References Cited

U.S. PATENT DOCUMENTS

| | | | |
|---|---|---|---|
| 4,175,057 A | 11/1979 | Davies et al. ............ 252/455 Z |
| 4,180,689 A * | 12/1979 | Davies et al. ............... 585/407 |
| 4,330,396 A | 5/1982 | Miller ........................ 208/16 |
| 4,377,503 A | 3/1983 | Dessau .................... 252/455 Z |
| 4,565,716 A | 1/1986 | Williams, Jr. et al. |
| 4,565,897 A | 1/1986 | Gane et al. ................. 585/415 |
| 4,613,716 A | 9/1986 | McNiff ....................... 585/415 |
| 4,642,403 A | 2/1987 | Hyde et al. ................. 585/415 |
| 4,663,025 A | 5/1987 | Fu ............................. 208/120 |
| 4,695,663 A | 9/1987 | Hall et al. .................. 585/417 |
| 4,832,824 A | 5/1989 | Vaughan et al. ............ 208/138 |
| 4,861,932 A | 8/1989 | Chen et al. .................. 585/42 |
| 4,882,040 A | 11/1989 | Dessa et al. ................ 208/138 |
| 4,922,051 A * | 5/1990 | Nemet-Mavrodin et al. ......................... 585/418 |
| 4,927,525 A | 5/1990 | Chu ........................... 208/138 |
| 4,982,028 A | 1/1991 | Dessau et al. .............. 585/277 |
| 4,990,715 A | 2/1991 | Know ......................... 585/417 |
| 5,013,423 A | 5/1991 | Chen et al. ................... 208/64 |
| 5,019,664 A * | 5/1991 | Del Rossi et al. .......... 585/419 |
| 5,149,679 A | 9/1992 | Price et al. ................... 502/61 |
| 5,220,086 A * | 6/1993 | Rodewald ................... 585/407 |
| 5,464,800 A | 11/1995 | Galperin et al. ............. 502/66 |

OTHER PUBLICATIONS

Applied Catalysis, vol. 131, No. 1, Oct. 1995, pp. 7–14.
Applied Catalysis, vol. 131, No. 2, Oct. 1995, pp. 347–369.

* cited by examiner

*Primary Examiner*—Nadine Norton

(57) ABSTRACT

A catalyst composition and a process for converting a hydrocarbon stream such as, for example, gasoline to $C_6$ to $C_8$ aromatic hydrocarbons such as toluene and xylenes are disclosed. The catalyst composition includes an alumina, a silica, and a metal wherein the weight ratio of aluminum to silicon is in the range of from about 0.002:1 to about 0.6:1. The process includes contacting a hydrocarbon stream with the catalyst composition under a condition sufficient to effect the conversion of a hydrocarbon to a $C_6$ to $C_8$ aromatic hydrocarbon. Also disclosed is a process for producing the catalyst composition which includes: (1) contacting a zeolite with an effective amount of an acid under a condition sufficient to effect a reduction in aluminum content of the zeolite to produce an acid-leached zeolite; and (2) impregnating the acid-leached zeolite with an effective amount of a metal compound under a condition sufficient to effect the production of a metal-promoted zeolite.

37 Claims, No Drawings

US 6,593,503 B1

PROCESS FOR MAKING AROMATIC HYDROCARBONS USING AN ACID TREATED ZEOLITE

FIELD OF THE INVENTION

This invention relates to a catalyst composition useful for converting a hydrocarbon to a $C_6$ to $C_8$ aromatic hydrocarbon, to a process for producing the composition, and to a process for using the composition for converting a hydrocarbon to a $C_6$ to $C_8$ aromatic hydrocarbon.

BACKGROUND OF THE INVENTION

It is well known to those skilled in the art that aromatic hydrocarbons are a class of very important industrial chemicals which find a variety of uses in petrochemical industry. It is also well known to those skilled in the art that catalytically cracking gasoline-range hydrocarbons produces aromatic hydrocarbons such as, for example, benzene, toluene, and xylenes (hereinafter collectively referred to as BTX) in the presence of catalysts which contain a zeolite. The product of this catalytic cracking process contains a multitude of hydrocarbons including unconverted $C_5+$ alkanes, $C_5+$ alkenes, $C_5+$ cycloalkanes, or combinations of two or more thereof; lower alkanes such as methane, ethane, and propane; lower alkenes such as ethylene and propylene; and $C_9+$ aromatic hydrocarbons. Recent efforts to convert gasoline to more valuable petrochemical products have therefore focused on improving the conversion of gasoline to more valuable aromatic hydrocarbons in the presence of zeolite catalysts. For example, a gallium-promoted zeolite ZSM-5 has been used in the so-called Cyclar Process to convert a hydrocarbon to BTX. The aromatic hydrocarbons can be useful feedstocks for producing various organic compounds and polymers. However, heavier, less useful aromatic compounds having 9 or more carbon atoms per molecule are also produced by the conversion process. Furthermore, a zeolite catalyst is generally deactivated in a rather short period because of depositions of carbonaceous material, generally coke, on the surface of the catalyst. Therefore, development of a catalyst and a process for converting non-aromatic hydrocarbons to the more valuable BTX in which the process and catalyst reduce the depositions of the carbonaceous material would be a significant contribution to the art and to the economy.

SUMMARY OF THE INVENTION

An object of this invention is to provide a catalyst composition which can be used to convert a hydrocarbon to a $C_6$ to $C_8$ aromatic hydrocarbon. Also an object of this invention is to provide a process for producing the catalyst composition. Another object of this invention is to provide a process which can employ the catalyst composition to convert a hydrocarbon to a $C_6$ to $C_8$ aromatic hydrocarbon. An advantage of the catalyst composition is that it enhances the production of BTX. Other objects and advantages will become more apparent as this invention is more fully disclosed hereinbelow.

According to a first embodiment of the present invention, a composition which can be used as a catalyst for converting a hydrocarbon or a hydrocarbon mixture to a $C_6$ to $C_8$ aromatic hydrocarbon is provided. The composition is an aluminosilicate which comprises, a silica, an alumina, and a metal selected from the group consisting of nickel, palladium, molybdenum, gallium, platinum and combinations of any two or more thereof wherein the weight ratio of elemental aluminum to elemental silicon is in the range of from about 0.002:1 to about 0.6:1 and the weight ratio of the metal to silicon is in the range of from about 0.0005:1 to about 0.1:1.

According to a second embodiment of the present invention, a process which can be used for producing a catalyst composition is provided. The process comprises the steps: (1) contacting a zeolite, which comprises or consists essentially of silicon and aluminum, with an acid in an amount and under a condition effective to reduce the aluminum content of the zeolite to produce an aluminum-reduced zeolite; (2) contacting said aluminum-reduced zeolite with a metal compound whose metal is selected from the group consisting of nickel, palladium, molybdenum, gallium, platinum, and combinations of any two or more thereof under a condition effective to impregnate the metal compound or the metal onto the aluminum-reduced zeolite to produce a metal-impregnated, alumina-reduced zeolite; and optionally (3) treating the metal-impregnated aluminum-reduced zeolite with a reducing agent under a condition effective to lower the oxidation state of the metal in the metal-impregnated, aluminum-reduced zeolite.

According to a third embodiment of the present invention, a process which can be used for converting a hydrocarbon or a hydrocarbon mixture to a $C_6$ to $C_8$ aromatic hydrocarbon for reducing the deposition of carbonaceous material on the surface of a catalyst is provided which comprises, consists essentially of, or consists of, contacting a fluid which comprises a hydrocarbon or a hydrocarbon mixture with a catalyst composition which is the same as disclosed above in the first embodiment of the invention under a condition effective to convert a hydrocarbon to an aromatic hydrocarbon containing 6 to 8 carbon atoms per molecule.

DETAILED DESCRIPTION OF THE INVENTION

The catalyst composition of the first embodiment of the present invention is an aluminosilicate which can comprise, consist essentially of, or consist of a coke-reducing amount of a metal selected from the group consisting of nickel, palladium, molybdenum, gallium, platinum, and combinations of any two or more thereof.

According to the present invention, the term "coke" refers to a semi-pure carbon generally deposited on the surface of a metal wall or a catalyst. The weight ratio of aluminum to silicon can be any ratio that is effective to convert an aliphatic hydrocarbon to an aromatic hydrocarbon. Generally, the weight ratio of element aluminum to element silicon can be in the range of from about 0.002:1 to about 0.6:1, preferably about 0.005:1 to about 0.5:1, and most preferably 0.006:1 to 0.4:1. The weight ratio of the metal to element silicon can be in the range of from about 0.0001:1 to about 0.1:1, preferably about 0.0005:1 to about 0.05:1, more preferably about 0.001:1 to about 0.04:1, and most preferably 0.002:1 to 0.03:1.

Alternatively, the weight of element aluminum in the invention composition can be in the range of from about 0.1 to about 10, preferably about 0.2 to about 8, and most preferably 0.5 to 5 grams per 100 grams of the composition. The weight of element silicon in the invention composition can be in the range of from about 20 to about 50, preferably about 25 to about 45, and most preferably 30 to 40 grams per 100 grams of the composition. The weight of the metal can be in the range of from about 0.001 to about 10, preferably about 0.01 to about 5, and most preferably 0.1 to 2 grams per 100 grams of the composition. The composition can also be characterized by having the following physical characteristics: a micropore surface area, as determined by the BET method using nitrogen, in the range of from about 250 to about 600, preferably 300 to 500 m$^2$/g; a micropore pore volume in the range of from about 0.01 to about 0.8, preferably about 0.01 to about 0.75 ml/g; an average micropore pore diameter in the range of from about 10 to about 300, preferably about 10 to about 250 Å; and a porosity of more than about 30%. Detailed physical property analyses are disclosed hereinbelow in the Examples section.

The aluminosilicate or zeolite component of the composition of the present invention can be prepared by combining any alumina and any silica in the element weight ratios disclosed above under any conditions sufficient to effect the formation of a zeolite according to any methods well known to one skilled in the art. However, it is presently preferred that the composition of the present invention be produced by the process disclosed in the second embodiment of the invention. In the first step of the second embodiment of the invention, a zeolite is contacted with an acid under a condition sufficient to effect the formation of an aluminum-reduced zeolite.

Any commercially available zeolites can be employed as a starting material of the process of the second embodiment of the invention. Examples of suitable zeolites include, but are not limited to, those disclosed in Kirk-Othmer Encyclopedia of Chemical Technology, third edition, volume 15 (John Wiley & Sons, New York, 1991) and in W. M. Meier and D. H. Olson, "Atlas of Zeolite Structure Types," pages 138–139 (Butterworth-Heineman, Boston, Mass., 3rd ed. 1992). ZSM-5 and similar zeolites that have been identified as having a crystalline framework topology or structure identified as MFI are particularly preferred because of their shape selectivity. A zeolite can further comprise or be combined with an inorganic binder such as alumina, silica, alumina-silica, aluminum phosphate, clay (such as, for example, bentonite), and combinations of any two or more thereof.

Generally, any organic acids, inorganic acids, or combinations of any two or more thereof can be used in the process of the present invention so long as the acid can reduce the aluminum content in the zeolite. The acid can also be a diluted aqueous acid solution. Examples of suitable acids include, but are not limited to sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids, wherein one or more protons have been replaced with, for example, a metal (preferably an alkali metal), and combinations of any two or more thereof. Examples of partially neutralized acids include, but are not limited to, sodium bisulfate, sodium dihydrogen phosphate, potassium hydrogen tartarate, and combinations thereof. The presently preferred acids are hydrochloric acid and nitric acid for they are readily available.

Any methods known to one skilled in the art for treating a solid catalyst with an acid can be used in the acid treatment of the present invention. Generally, a zeolite material can be suspended in an acid solution. The concentration of the zeolite in the acid solution can be in the range of from about 0.01 to about 500, preferably about 0.1 to about 400, more preferably about 1 to about 350, and most preferably 5 to 300 grams per liter. The amount of acid required is the amount that can maintain the solution in acidic pH during the treatment. Preferably the initial pH of the acid solution containing a zeolite is adjusted to lower than about 6, preferably lower than about 4, more preferably lower than about 3, and most preferably lower than 2. Upon the pH adjustment of the solution, the solution can be subjected to a treatment at a temperature in the range of from about 30° C. to about 200° C., preferably about 50° C. to about 150° C., and most preferably 70° C. to 120° C. for about 10 minutes to about 30 hours, preferably about 30 minutes to about 25 hours, and most preferably 1 to 20 hours. The treatment can be carried out under a pressure in the range of from about 1 to about 10 atmospheres (atm), preferably about 1 atm. Thereafter, the acid-treated zeolite material can be washed with a running water for 1 to about 60 minutes followed by drying, at about 50 to about 200, preferably about 75 to about 175, and most preferably 100 to 150° C. for about 0.5 to about 15, preferably about 1 to about 12, and most preferably 1 to 10 hours, to produce an aluminum-reduced or acid-leached zeolite. Any drying method known to one skilled in the art such as, for example, air drying, heat drying, spray drying, fluidized bed drying, or combinations of two or more thereof can be used.

The dried, aluminum-reduced zeolite can also be further washed, if desired, with a mild acid solution such as, for example, ammonium nitrate which is capable of maintaining the pH of the wash in acidic range. The volume of the acid generally can be the same volume as the acid for reducing the alumina content in a zeolite. The mild acid treatment can be carried out under substantially the same conditions disclosed in the acid treatment for reducing alumina content in a zeolite. Thereafter, the resulting solid can be washed and dried as disclosed above.

The dried, aluminum-reduced zeolite, whether it has been further washed with a mild acid or not, can be calcined under a condition known to those skilled in the art. Generally such a condition can include a temperature in the range of from about 250 to about 1,000, preferably about 350 to about 750, and most preferably 450 to 650° C. and a pressure in the range of from about 0.5 to about 50, preferably about 0.5 to about 30, and most preferably 0.5 to 10 atmospheres (atm) for about 1 to about 30 hours, preferably about 2 to about 20 hours, and most preferably 3 to 15 hours.

Thereafter, the aluminum-reduced zeolite, whether it has been calcined or not, is impregnated thereon with a metal compound whose a metal selected from the group consisting of nickel, palladium, molybdenum, gallium, platinum, and combinations of any two or more thereof. Any metal compound that can promote the impregnating of the aluminum-reduced zeolite with the metal of the metal compound can be employed in the present invention. Examples of such metal compounds include, but are not limited to, nickel chloride, nickel bromide, nickel nitrate, nickel sulfate, nickel hydroxide, palladium chloride, palladium nitrate, palladium sulfate, palladium acetate, palladium hydroxide, molybdenum chloride, molybdenum bromide, chloroplatinic acid ($H_2PtCl_6 \cdot xH_2O$), platinum (IV) chloride (platinic chloride), platinum (II) bromide, platinum (II) iodine, tetramine platinum (II) chloride ($Pt(NH_3)_4Cl_2 \cdot H_2O$ or $Pt(NH_3)_4Cl_2$), tetramine platinum (II) nitrate ($Pt(NH_3)_4(NO_3)_2$), tetramine platinum (II) hydroxide ($Pt(NH_3)_4(OH)_2$), tetrachlorodiamine platinum (IV), gallium acetate (basic), gallium trifluoride, gallium trichloride, gallium, gallium hydroxide, gallium nitrate, gallium sulfate, and combinations of any two or more thereof. The presently preferred metal compounds are chloroplatinic acid and gallium nitrate for they are readily available.

A metal-promoted or metal-impregnated, aluminum-reduced zeolite can be prepared by any suitable, effective means so long as the resulting zeolite can be used in the process of the present invention. Preferably, the aluminum-reduced or acid-leached zeolite, which can have been compounded with a binder as described above and have been shaped by any means known in the art such as, for example, pelletized, extruded, tableted, or combinations of two or more thereof, can be impregnated such as, for example, by incipient wetness method with a solution, preferably aqueous solution, containing a suitable metal compound disclosed above. The concentrations of the metal compound in the impregnating solution and the weight ratio of this solution to the zeolite are chosen such as to provide a finished, metal-impregnated, aluminum-reduced zeolite which contains the desired content of metal which can effect the reduction of coke deposition on the surface of the composition of the present invention as disclosed above in the first embodiment of the present invention.

After the impregnation with a metal compound has been completed, the metal-impregnated, aluminum-reduced zeolite can then be dried, as disclosed above and then calcined. Generally the calcination is carried out in air under the pressure range disclosed above for calcining the aluminum-reduced zeolite. The calcination can also be carried out at a temperature in the range of about 300 to about 1000° C. for about 1 to about 30 hours, preferably about 400° C. to about 800° C. for 2 to about 20 hours, and most preferably 450° C. to 650° C. for 3 to 15 hours.

The calcined metal-impregnated, aluminum-reduced zeolite can then be treated with a reducing agent to reduce the oxidation state of the metal. For example, if the metal is platinum, the oxidation state of platinum is reduced to 0 whereas gallium's oxidation state can be reduced to 1. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 550° C. for 1 to 5 hours. If the calcined metal-impregnated, aluminum-reduced zeolite is not first treated with a reducing agent, the composition of the present invention can be treated with a reducing agent as described herein prior to use of the composition of the invention.

Upon completion of the above-described treatment or impregnation of an aluminum-reduced or acid-leached zeolite with a metal compound, a metal-promoted zeolite composition is produced which can then be used in the third embodiment of the present invention.

According to the third embodiment of the present invention, a process useful for converting an aliphatic hydrocarbon or a hydrocarbon mixture to a mixture rich in $C_6$ to $C_8$ aromatic hydrocarbons comprises, consists essentially of, or consists of contacting a fluid stream with a catalyst composition, optionally in the presence of a hydrogen-containing fluid, under a condition sufficient to enhance or effect the conversion of a hydrocarbon to a mixture rich in $C_6$ to $C_8$ aromatic hydrocarbons wherein said fluid stream comprises a hydrocarbon or hydrocarbon mixture which comprises paraffins, olefins, naphthenes. Aromatic compounds can also be present in the fluid in some minor amounts. The catalyst composition is the same as that disclosed in the first embodiment of the invention which can be prepared by the second embodiment of the invention.

The term "fluid" is used herein to denote gas, liquid, vapor, or combinations thereof. The term "hydrocarbon" is generally referred to, unless otherwise indicated, as one or more hydrocarbons having from about 4 carbon atoms to about 25 carbon atoms, preferably about 5 to about 20 carbon atoms, and most preferably 5 to 16 carbon atoms per molecule. The term "enhance" refers to an increased BTX in the product employing the catalyst composition as compared to employing a non-acid-leached zeolite. Examples of a hydrocarbon include, but are not limited to, butane, isobutanes, pentane, isopentanes, hexane, isohexanes, cyclohexane, methylcyclohexane, heptane, isoheptanes, octane, isooctanes, nonanes, decanes, undecanes, dodecanes, tridecanes, tetradecanes, pentadecanes, hexadecanes, butenes, isobutene, pentenes, hexenes, and combinations of any two or more thereof. In some feed fluids, such as, for example, gasoline can comprise some benzene, toluene, ethylbenzene, and xylenes.

Any fluid which contains a hydrocarbon as disclosed above can be used as the feed for the process of this invention. Generally, the fluid feed stream can also contain olefins, naphthenes (cycloalkanes), or some aromatic compounds. Examples of suitable, available fluid feeds include, but are not limited to, gasolines from catalytic oil cracking processes, pyrolysis gasolines from thermal cracking of saturated hydrocarbons, naphthas, gas oils, reformates, and combinations of any two or more thereof. The origin of this fluid feed is not critical. Though particular composition of a feed is not critical, a preferred fluid feed is derived from gasolines which generally contain more paraffins (alkanes) than combined content of olefins, cycloalkanes, and aromatic compounds.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid feed stream containing a hydrocarbon with a hydrogen-containing fluid in the presence of the catalyst composition can be carried out in any technically suitable manner, in a batch or semicontinuous or continuous process, under a condition effective to convert a hydrocarbon to a $C_6$ to $C_8$ aromatic hydrocarbon. Generally, a fluid stream as disclosed above, preferably being in the vaporized state, is introduced into an aromatization reactor having a fixed catalyst bed, or a moving catalyst bed, or a fluidized catalyst bed, or combinations of any two or more thereof by any means known to one skilled in the art such as, for example, pressure, meter pump, and other similar means. Because an aromatization reactor and aromatization process are well known to one skilled in the art, the description of which is omitted herein for the interest of brevity. The condition of the process of the invention can include a weight hourly space velocity (WHSV) of the fluid feed stream in the range of about 0.01 to about 100, preferably about 0.05 to about 50, and most preferably 0.1 to 30 g feed/g catalyst/hour. The hydrogen-containing fluid (gas) hourly space velocity generally is in the range of about 1 to about 10,000, preferably about 5 to about 7,000, and most preferably 10 to 5,000 ft$^3$ H$_2$/ft$^3$ catalyst/hour. Generally, the pressure can be in the range of from about 0 to about 1000 psig, preferably about 0 to about 200 psig, and most preferably 0 to 100 psig, and the temperature is about 250 to about 1000° C., preferably about 300 to about 750° C., and most preferably 400 to 650° C.

The process effluent generally contains a light gas fraction comprising hydrogen and methane; a $C_2$–$C_3$ fraction containing ethylene, propylene, ethane, and propane; an intermediate fraction including non-aromatic compounds higher than 3 carbon atoms; a BTX aromatic hydrocarbons fraction (benzene, toluene, ortho-xylene, meta-xylene and para-xylene); and a $C_9$+ fraction which contains aromatic compounds having 9 or more carbon atoms per molecule. Generally, the effluent can be separated into these principal fractions by any known methods such as, for example, fractionation distillation. Because the separation methods are well known to one skilled in the art, the description of which is omitted herein. The intermediate fraction can be recycled to an aromatization reactor described above; methane, ethane, and propane can be used as fuel gas or as a feed for other reactions such as, for example, in a thermal cracking process to produce ethylene and propylene. The olefins can be recovered and further separated into individual olefins by any method known to one skilled in the art. The individual olefins can then be recovered and marketed. The BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes) involving transalkylation benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the desired ratios of olefins to BTX have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 1000° C. The optimal time periods of the calcining depend generally on the types and amounts of deactivating deposits on the catalyst composition and on the calcination temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the effect of the treatment of a ZSM-5 zeolite material with an inorganic acid, essentially in accordance with the first step of the catalyst preparation method of this invention.

Zeolite Material A was a commercial ZSM-5 material, which had been provided by UOP (Des Plains, Ill. 60017) as 1/16 inch extrudates under the product designation "MFI-38". This material was calcined in air for about 6 hours at 525° C.

Zeolite Material B was prepared by treating 30.0 g (40 ml) of Zeolite Material A with 100 g of an aqueous, 6N HCl solution (i.e., an aqueous solution containing 6 g-equivalents of hydrogen chloride) for 2 hours at 85° C. The mixture of acid-treated zeolite material and HCl solution was filtered. The separated acid-treated zeolite material was washed with water, dried, and calcined in air for about 6 hours at about 500° C.

The following pertinent properties of Zeolite Material A (not acid-treated) and of Zeolite Material B (treated with 6N HCl) were determined.

(1) The Si:Al atomic ratio in the crystalline zeolite framework, referred to as $(Si:Al)_c$, was determined by solid-state $^{29}Si$ and $^{27}Al$ NMR analyses (substantially in accordance with a procedure referred to in U.S. Pat. No. 4,663,025, column 4, lines 25–32; disclosure of the U.S. patent is incorporated herein by reference) employing an IBM/Bruker WP200 SY spectrometer, equipped with a Tecmag Aries system control unit and a Chemagnetics MAS probe. About 250 mg of each zeolite material was packed into a 7.5 mm zirconia rotor and spun at 7.0 KHz. For Si-29 NMR (at 39.75 MHZ), a single pulse sequence with a 45° flip angle and a repetition delay of 20 seconds was used. For Al-27 NMR (at 52.15 MHZ), a single pulse with a 30° flip angle and a 1 second delay was used. TMS (tetramethylsilane) was used as an internal chemical shift reference at 0 ppm for Si-29.

(2) The Si:Al atomic ratios of the entire (total) zeolite materials (including the crystalline zeolite framework, amorphous silica and alumina, and binder), referred to as $(Si:Al)_t$, were also determined. This determination was carried out by fluorescence spectrometry (substantially in accordance with the procedure referred to in U.S. Pat. No. 4,663,025, column 4, lines 36–44).

(3) The surface area of the zeolite materials was determined by the Brunauer, Emmett and Teller (BET) method using nitrogen (substantially in accordance with the procedure referred to in U.S. Pat. No. 4,663,025, column 4, lines 45–51).

(4) The pore structure of the zeolite materials were determined by mercury intrusion porosimetry (substantially in accordance with the procedure referred to in U.S. Pat. No. 4,975,399, column 2, lines 38–46; disclosure of the U.S. patent is incorporated herein by reference).

Pertinent test results are summarized in Table I.

TABLE I

| | Zeolite Material A | Zeolite Material B |
|---|---|---|
| Atomic Ratio $(Si:Al)_c$ | 22.0:1 | 25.7:1 |
| Atomic Ratio $(Si:Al)_t$ | 2.4:1 | 18.3:1 |
| Total (BET) Surface area (m²/g) | 378 | 386 |
| Micropore[1] Surface Area (m²/g) | 265 | 313 |
| Mesopore[2] Surface Area (m²/g) | 113 | 73 |
| Micropore[1] Pore Volume (ml/g) | 0.108 | 0.126 |
| Mespore[2] Pore Volume (ml/g) | 0.305 | 0.436 |
| Avg. Micropore[1] Radius (Å) | 17 | 15 |
| Avg. Mesopore[2] Radius (Å) | 84 | 241 |

[1]Size of micropores: <20 Å
[2]Size of mesopores: 200–500 Å
Note: Macropores (>500 Å) were not found.

Test data in Table I show that the treatment of the zeolite starting material (Zeolite Material A) with 6N HCl had significant effect on $(Si:Al)_c$, i.e., the Si:Al atomic ratio of the crystalline zeolite framework, as well as $(Si:Al)_t$, i.e., the total Si:al atomic ratio. For example, a significant increase in $(Si:Al)_t$ from 2.4:1 to about 18.3:1 was observed. These results indicate that the 6N HCl acid solution removed a portion of aluminum from the crystalline zeolite portion but leached out a substantial amount of amorphous alumina.

Test data in Table I further show that only relatively minor changes in the micropore pore parameters (surface area, volume and radius) were caused by the treatment with 6N HCl, whereas significant changes in mesopore parameters (surface area, volume and radius) resulted from this treatment. It is particularly noteworthy that the average pore radius of micropores remained virtually unchanged by the HCl treatment, whereas the average pore radius of the HCl-treated (acid-leached) Zeolite Material B was about three times higher than that of the untreated Zeolite Material A.

EXAMPLE II

This example illustrates the effectiveness of various acid solutions in the acid treatment of a ZSM-5 zeolite material.

Zeolite Material C was obtained essentially in accordance with the procedure for preparing Zeolite Material B (described in Example I), except that 15.0 g (20 ml) of Zeolite Material A was treated with 100 g of the aqueous 1N HCl solution.

Zeolite Material D was obtained essentially in accordance with the procedure for preparing Zeolite Material C, except that 100 g of an aqueous 6N HCl was used. This material is substantially the same as Zeolite Material B.

Zeolite Material E was obtained essentially in accordance with the procedure for preparing Zeolite Material C, except that 100 g of aqueous 10N HCl was used.

Zeolite Material F was obtained essentially in accordance with the procedure for preparing Zeolite Material C, except that 100 g of an aqueous 8N $HNO_3$ was used.

Pertinent properties of these Zeolite Materials are summarized in Table II.

TABLE II

| Zeolite Material | Acid Solution Employed | Total Pore Volume ($M^1$/g) | Total Si:Al Atomic Ratio |
|---|---|---|---|
| A | none | 0.53 | 2.4:1 |
| C[1] | 1N HCl | 0.53 | 2.7:1 |
| D[1] | 6N HCl | 0.67 | 18:1 |
| E[2] | 10N HCl | 0.67 | 56:1 |
| F[1] | 8N $HNO_3$ | 0.53 | 2.4:1 |

[1]Retained the structural integrity (i.e., the cylindrical shape of extrudates) of the starting zeolite material.
[2]Disintegrated into a powder.

Test results in Table II indicate that the aqueous 6N HCl solution was best suited as the acid solution for the acid treatment step of the catalyst preparation in accordance with this invention. Significant increases in pore volume and in total Si:Al atomic ratio (versus the starting material, Zeolite Material A) were attained with 6N HCl, while the structural integrity of the obtained acid-treated material was retained. Treatments with 1N HCl and 8N $HNO_3$ solutions were relatively less effective. Treatment with 10N HCl caused the extrudate particles to substantially disintegrate. Based on the above test results, it is concluded that aqueous HCl solutions having a concentration of about 1 to about 9, preferably about 2 to about 9, and most preferably 3 to 8 g-equivalents HCl per liter solution are the most effective treating solutions for the acid treatment step of the preparation method of this invention.

EXAMPLE III

This example illustrates the preparation of several gallium-promoted, HCl-treated ZSM-5 zeolite materials.

Catalyst 1 (Invention) was prepared as follows. A sample of 18.0 g of Zeolite Material D (i.e., Zeolite Material A which had been leached with a 6N HCl solution, as described in Example II) was impregnated (by the incipient wetness method) with 11.9 g of 20 weight % solution of $Ga(NO_3)_3.9H_2O$ in water. The thus-impregnated material was dried (first for 3 hours at room temperature and then for 3 hours at 125° C.). The dried material was calcined in air for 6 hours at 500° C., and finally treated (reduced) with flowing hydrogen gas for 2 hours at 450° C. Catalyst 1 contained 2.2 weight % Ga.

Catalyst 2 (Invention) was prepared essentially in accordance with the procedure for Catalyst 1, except that the final reducing treatment with hydrogen gas was carried out for 6 hours at 600° C. Catalyst 2 contained 2.2 weight % Ga.

Catalyst 3 (Invention) was prepared essentially in accordance with the procedure for Catalyst 2, except that the final reducing treatment step with hydrogen gas had been omitted. Catalyst 3 contained 2.2 weight % Ga.

Catalyst 4 was prepared substantially in accordance with the procedure for Catalyst 1, except that the starting material for the impregnation with gallium nitrate was Zeolite Material F which was Zeolite Material A leached with a 8N $HNO_3$ solution, as described in Example II. Catalyst 4 contained 2.2 weight % Ga.

Catalyst 5 (Control) was prepared as follows. A sample of 25.0 g of Zeolite Material A which was not acid-leached was impregnated with an aqueous impregnating solution containing 1.75 g of $Ga(NO_3)_3.9H_2O$ and 70 g of $HNO_3$-acidified water. The pH of the impregnating solution was 1.2. The mixture of Zeolite Material A and the impregnating solution was kept at 90° C. for about 16 hours. Thereafter, the Ga-impregnated zeolite material was separated from the solution, washed with water, and dried for 3 hours at 125° C. The dried material was calcined in air for 6 hours at 525° C. Finally, the calcined material was treated with flowing hydrogen gas for 2 hours at 500° C., and cooled in $H_2$ to 200° C.

Catalyst 6 (Control) was prepared by impregnating 12.0 g of Zeolite Material A (not acid-leached) with an impregnating solution containing 0.80 g of $Ga(NO_3)_3.9H_2O$ and 4.00 g of water, drying the Ga-impregnated material (first for 3 hours at room temperature; then for 3 hours at 125° C.), and calcining the dried material in air for 6 hours at 500° C. Catalyst 6 contained 1.1 weight-% Ga.

Catalyst 7 (Control) was essentially the same as Zeolite Material C as described in Example II, except that the treatment with the 6N HCl solution at 85° C. was carried out for 16 hours. Catalyst 7 contained no Ga.

EXAMPLE IV

This example illustrates the use of the catalysts described in Example III in the aromatization of a paraffinic hydrocarbon feed so as to produce a product containing a higher concentration of BTX (benzene, toluene, xylenes) than the feed.

The aromatization tests were carried out with n-pentane as the feed. A stainless-steel reactor tube (inner diameter: 2.5 cm; length: 50 cm) was filled with a 20 ml bottom layer of Alundum® alumina (inert, low surface area alumina, provided by Norton Company, Worcester, Mass.), 15 ml of one of the tested catalysts described in Example III, and a 20 ml top layer of Alundum®. The reactor and its content were heated from room temperature to the desired reaction temperature of about 450° C. within a time period of about 0.5 hour, with helium gas flowing through the rector (flow rate:

about 30 1/hour). The reaction pressure was about 50 psig. A liquid n-pentane feed was introduced into the heated reactor at a rate of about 60 ml/hour, which was equivalent to a liquid hourly space velocity (LHSV) of 4 ml/ml catalyst/hour. The product, which exited the reactor in the gaseous state, was analyzed by means of a gas chromatograph. Pertinent test results are summarized in Table III.

described in Example II) was impregnated (by the incipient wetness method) with 10.1 g of a solution containing 2.0 weight % hexachloroplatinic acid ($H_2PtCl_6$), 1.0 weight % $HNO_3$ and 97.0 weight % $H_2O$. The thus-impregnated material was dried (first for 6 hours at room temperature and then for 3 hours at 125° C.). The dried material was calcined in air for 6 hours at 525° C., and finally treated (reduced)

TABLE III

| | Catalyst Preparation | | | Time on | Wt-% of Components in Product | | | |
|---|---|---|---|---|---|---|---|---|
| Catalyst | Acid-Leaching | Ga Promotion | $H_2$ Treatment | Stream | $C_1$–$C_4$ | n-Pentane | BTX[2] | Heavies[3] |
| 1 | with 6N HCl | Yes | Yes (450° C.) | 2 Hours | 10.3 | 0.9 | 79.0 | 9.2 |
| | | | | 6 Hours | 10.1 | 1.0 | 79.3 | 8.9 |
| 2 | with 6N HCl | Yes | Yes (600° C.) | 2 Hours | 11.9 | 0.9 | 77.8 | 9.0 |
| | | | | 6 Hours | 11.6 | 1.2 | 78.0 | 8.7 |
| 3 | with 6N HCl | Yes | No | 2 Hours | 10.4 | 0.3 | 77.7 | 11.3 |
| | | | | 6 Hours | 12.8 | 0.7 | 76.3 | 9.4 |
| 4 | with 8N $HNO_3$ | Yes | Yes (450° C.) | 2 Hours | 13.7 | 0.8 | 67.6 | 16.6 |
| | | | | 6 Hours | 14.5 | 1.3 | 63.7 | 18.7 |
| 5 | No | Yes | Yes (500° C.) | 2 Hours | 15.2 | 0.9 | 69.7 | 13.3 |
| | | | | 6 Hours | 14.6 | 1.9 | 62.9 | 18.3 |
| 6 | No | Yes | No | 2 Hours | 18.1 | 0.9 | 67.3 | 12.7 |
| | | | | 6 Hours | 21.3 | 3.4 | 60.7 | 11.6 |
| 7 | with 6N HCl | No | No | 2 Hours | 14.3 | 0.6 | 67.3 | 16.6 |
| | | | | 6 Hours | 18.8 | 0.9 | 64.7 | 13.6 |

Test data in Table III clearly show that those catalyst which had been prepared by leaching with an aqueous 6N HCl solution and impregnation with gallium (i.e., Catalyst 1–3) were considerably more effective in converting n-pentane feed to desirable BTX (benzene, toluene, xylenes) than various control catalysts that were prepared by other methods such as Catalysts 5–7. Invention Catalysts 1–3 also retained their catalytic activity longer (as indicated by the BTX yields at 6 hours and 2 hours, respectively) than control Catalysts 5–7.

A comparison of the results for Catalysts 1 and 2 versus those for Catalyst 3 further indicates that a final reducing step with hydrogen (most preferably at about 450° C.) is preferred for attaining the highest yield of BTX. Based on the above results, it is concluded that the preparation comprising an acid-leaching step, in accordance with the preparation method of this invention, with an aqueous solution containing about 3–8 g-equivalents of HCl per liter solution (i.e., 4–8N HCl) produces the most active and most stable catalysts for converting non-aromatic hydrocarbons (in particular paraffins) to BTX aromatics.

EXAMPLE V

This example illustrates the preparation of a platinum-promoted, HCL-treated ZSM-5 zeolite material.

Catalyst 8 (Invention) was prepared as follows. A sample of 17.9 g (30 ml) of Zeolite Material D (i.e., Zeolite Material A which had been leached with a 6N HCl solution, as with flowing hydrogen gas for 2 hours at 425° C. Catalyst 8 contained 0.44 weight % Pt.

Catalyst 9 (Control) was prepared substantially in accordance with the procedure for Catalyst 8, except that 14.0 g Zeolite Material A (not acid-leached) was used (in lieu of acid-leached Zeolite Material D) as the starting material, and about 5.0 g of an impregnating solution containing 2.0 weight % $H_2PtCl_5$, 2.0 weight % HCl and 96.0 weight-% $H_2O$ was employed. The drying, calcining and reducing steps were carried out essentially in accordance with the procedure for Catalyst 8. Catalyst 9 contained 0.28 weight % Pt.

EXAMPLE VI

This example illustrates the use of the catalysts described in Example V in the aromatization of a gasoline-type hydrocarbon feed so as to produce BTX hydrocarbons (benzene, toluene, xylenes).

The aromatization tests were carried out substantially in accordance with the procedure described in Example IV, except that the liquid feed was not n-pentane but a gasoline which had been produced in a FCC cracking unit of Phillips Petroleum Company, Bartlesville, Okla. The composition of this gasoline feed is shown in Table IV.

TABLE IV

| | Hydrocarbon Analysis Cat Cracked Gasoline | | | | | |
|---|---|---|---|---|---|---|
| | n-paraffins | Isoparaffins | Aromatics | Naphthenes | Olefins | Total |
| $C_1$ | 0.000 | 0.000 | 0.000 | 0.000 | 0.000 | 0.000 |
| $C_2$ | 0.000 | 0.000 | 0.000 | 0.000 | 0.000 | 0.000 |
| $C_3$ | 0.000 | 0.000 | 0.000 | 0.000 | 0.000 | 0.000 |
| $C_4$ | 0.000 | 0.000 | 0.000 | 0.000 | 0.018 | 0.018 |
| $C_5$ | 1.292 | 8.147 | 0.000 | 0.169 | 10.741 | 20.348 |

TABLE IV-continued

Hydrocarbon Analysis Cat Cracked Gasoline

|  | n-paraffins | Isoparaffins | Aromatics | Naphthenes | Olefins | Total |
|---|---|---|---|---|---|---|
| $C_6$ | 0.749 | 7.164 | 1.266 | 1.972 | 7.135 | 18.287 |
| $C_7$ | 0.740 | 4.576 | 5.354 | 2.746 | 6.483 | 19.899 |
| $C_8$ | 0.760 | 3.234 | 8.120 | 2.531 | 0.830 | 15.475 |
| $C_9$ | 0.187 | 2.070 | 8.187 | 0.708 | 0.125 | 11.278 |
| $C_{10}$ | 0.163 | 1.193 | 5.155 | 0.072 | 0.048 | 6.631 |
| $C_{11}$ | 0.153 | 0.307 | 3.606 | 0.191 | 0.000 | 4.257 |
| $C_{12}$ | 0.115 | 0.974 | 0.768 | 0.088 | 0.000 | 1.946 |
| $C_{13}$ | 0.048 | 0.000 | 0.000 | 0.000 | 0.000 | 0.048 |
| $C_{14}$ | 0.000 | 0.000 | 0.000 | 0.000 | 0.000 | 0.000 |
| Total | 4.208 | 27.664 | 32.457 | 8.478 | 23.381 | 98.188 |
|  |  |  |  |  | Total $C_{15}+$ | 0.108 |
|  |  |  |  |  | Total Unknown: | 1.704 |

Each catalyst was pretreated with flowing hydrogen gas (flow rate: 500 ml/minute) before it was used in the aromatization tests. The liquid gasoline feed was introduced at a rate of about 40 ml/hour, together with about 260 ml/minute $H_2$ gas as cofeed (so as to attain a molar ratio of $H_2$ to hydrocarbons of about 2:1). The reaction temperature was about 450° C., and the reaction pressure was about 50 psig. The entire produce which exited the reactor was analyzed by means of a gas chromatograph. Pertinent test results are summarized in Table V.

TABLE V

| Catalyst | Catalyst Preparation | | | Time on Stream | Wt-% of Component in Product | | |
|---|---|---|---|---|---|---|---|
|  | Acid-Leaching | Pt Promotion | $H_2$ Treatment |  | $C_1$–$C_4$ | BTX[2] | Heavies[3] |
| 8 (Invention) | with 6N HCl | Yes | Yes (425° C.) | 2 Hours | 7.4 | 78.6 | 13.9 |
|  |  |  |  | 6 Hors | 7.8 | 76.4 | 15.8 |
| 9 (Control) | No | Yes | Yes (425° C.) | 2 Hours | 12.7 | 71.4 | 15.9 |
|  |  |  |  | 6 Hours | 14.6 | 67.4 | 18.0 |

[1]Paraffins and olefins containing 1–4 carbon atoms per molecule.
[2]Benzene, toluene, o-xylene, m-xylene, p-xylene.
[3]Mainly aromatic hydrocarbons containing 9 or more than 9 carbon atoms per molecule.

Test data in Table V clearly show that Invention Catalyst 8, which had been prepared by a method comprising acid-leaching with a 6N HCl solution, was considerably more effective in converting gasoline to desirable BTX hydrocarbons and was also more stable than Control Catalyst 9 (prepared without an acid treatment step). Invention Catalyst 8 produced smaller amounts of less desirable lights and heavies than Control Catalyst 9. Based on the above results, it is concluded that Pt-promoted zeolite catalysts which had undergone acid-leaching with an about 4–8N HCl solution before impregnation with Pt are the most effective and stable catalyst for converting nonaromatic hydrocarbons to BTX aromatics.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

What is claimed is:

1. A process comprising contacting a fluid which comprises a hydrocarbon with a catalyst composition under a condition sufficient to effect the conversion of a hydrocarbon to an olefin and a $C_6$ to $C_8$ aromatic hydrocarbon wherein said catalyst composition comprises a ZSM-5 zeolite and a metal selected from the group consisting of nickel, palladium, molybdenum, gallium, platinum, and combinations of any two or more thereof; and said zeolite is treated with an acid before being incorporated with said metal.

2. A process according to claim 1 wherein said fluid is selected from the group consisting of gasolines from catalytic oil cracking processes, pyrolysis gasolines from thermal cracking of saturated hydrocarbons, naphthas, gas oils, reformates, and combinations of any two or more thereof.

3. A process according to claim 1 wherein said hydrocarbon contains about 4 to about 30 carbon atoms.

4. A process according to claim 1 wherein said hydrocarbon contains 5 to 16 carbon atoms.

5. A process according to claim 1 wherein said hydrocarbon is selected from the group consisting of butane, isobutanes, pentane, isopentanes, hexane, isohexanes, cyclohexane, heptane, isoheptanes, octane, isooctanes, nonanes, decanes, undecanes, dodecanes, tridecanes, tetradecanes, pentadecanes, hexadecanes, butenes, isobutene, pentenes, hexenes, and combinations of any two or more thereof.

6. A process according to claim 1 wherein said hydrocarbon is a gasoline.

7. A process according to claim 1 wherein said hydrocarbon is a n-pentane.

8. A process according to claim 1 wherein the weight ratio of aluminum to silicon in said zeolite is in the range of from about 0.005:1 to about 0.5:1.

9. A process according to claim 1 wherein the weight ratio of aluminum to silicon in said zeolite is in the range of from 0.006:1 to 0.4:1.

10. A process according to claim 1 wherein the weight ratio of said metal to silicon in said zeolite is in the range of from about 0.001:1 to about 0.04:1.

11. A process according to claim 1 wherein the weight ratio of said metal to silicon in said zeolite is in the range of from 0.002:1 to 0.03:1.

12. A process according to claim 1 wherein said condition comprises a liquid hourly space velocity of said fluid in the range of about 0.01 g/g catalyst/hour to about 100 g/g catalyst/hour, a pressure in the range of about 0 psig to about 200 psig, and a temperature in the range of about 250° C. to about 1,000° C.

13. A process according to claim 1 wherein said condition comprises a liquid hourly space velocity of said fluid in the range of 0.1 g/g catalyst/hour to 30 g/g catalyst/hour, a pressure in the range of 0 psig to 100 psig, and a temperature in the range of 450° C. to 650° C.

14. A process according to claim 1 wherein said metal is platinum.

15. A process according to claim 1 wherein said metal is gallium.

16. A process according to claim 1 wherein the weight of elemental aluminum in said zeolite is in the range of from about 0.1 to about 10 grams per 100 grams of said composition, the weight of elemental silicon in said zeolite is in the range of from about 20 to about 50 g per 100 grams of said composition, and the weight of said metal in said zeolite is in the range of from about 0.001 to about 10 g per 100 grams of said composition.

17. A process comprising contacting a hydrocarbon with a catalyst composition under a condition sufficient to effect the conversion of said hydrocarbon to a $C_6$ to $C_8$ aromatic hydrocarbon wherein said composition is prepared by the steps of: (1) contacting a zeolite with an aqueous solution containing an acid at a pH lower than about 6, at a temperature in the range of from about 30 to about 200° C., under about 1 to about 10 atm pressure, and for a period of from about 10 minutes to about 30 hours to produce an aluminum-reduced zeolite; (2) contacting said aluminum-reduced zeolite with a metal compound under conditions sufficient to produce a metal-promoted zeolite; and (3) calcining said metal-promoted zeolite wherein the metal of said metal compound is selected from the group consisting of nickel, palladium, molybdenum, gallium, platinum, and combinations of any two or more thereof; and said acid is selected from the group consisting of sulfuric acid, hydrochloric acid, nitric acid, phosphoric acid, ammonium sulfate, ammonium chloride, ammonium nitrate, formic acid, acetic acid, trifluoroacetic acid, citric acid, trichloroacetic acid, p-toluenesulfonic acid, methanesulfonic acid, partially neutralized acids, and combinations of any two or more thereof.

18. A process according to claim 17 wherein step (1) is carried out in a hydrochloric acid solution wherein the concentration of hydrochloric acid is in the range of from about 1 to about 9 gram-equivalents per liter solution (about 1 to about 9N HCl).

19. A process according to claim 18 wherein the concentration of hydrochloric acid in the acid solution is in the range of from about 2 to about 9 gram equivalents.

20. A process according to claim 18 wherein the concentration of hydrochloric acid in the acid solution is in the range of from 3 to 8 gram equivalents.

21. A process according to claim 18 wherein the metal is selected from the group consisting of gallium, platinum, and combinations thereof.

22. A process according to claim 18 wherein said metal is gallium.

23. A process according to claim 18 wherein said metal is platinum.

24. A process according to claim 17 wherein said contacting of said hydrocarbon is carried out in the presence of a hydrogen-containing fluid.

25. A process according to claim 18 wherein said contacting of said hydrocarbon is carried out in the presence of a hydrogen-containing fluid.

26. A process according to claim 25 wherein said hydrogen-containing fluid is hydrogen.

27. A process according to claim 18 wherein said condition for converting said hydrocarbon comprises a liquid hourly space velocity of said fluid in the range of 0.1 g/g catalyst/hour to 30 g/g catalyst/hour, a pressure in the range of 0 psig to 50 psig, and a temperature in the range of 450° C. to 650° C.

28. A process according to claim 18 wherein said hydrocarbon comprises gasolines from catalytic oil cracking processes, pyrolysis gasolines from thermal cracking of saturated hydrocarbons, naphthas, gas oils, reformates, and combinations of any two or more thereof.

29. A process according to claim 18 wherein said hydrocarbon is gasoline.

30. A process according to claim 18 wherein said hydrocarbon is n-pentane.

31. A process for converting a gasoline or pentane to an aromatic hydrocarbon comprising contacting said gasoline or pentane with a catalyst composition wherein said process is carried out at a liquid hourly space velocity of said fluid in the range of 0.1 g/g catalyst/hour to 30 g/g catalyst/hour, a pressure in the range of 0 psig to 50 psig, and a temperature in the range of 450° C. to 650° C.;

said aromatic hydrocarbon comprises at least one $C_6$ to $C_8$ aromatic compound; and said catalyst is prepared by the steps of: (1) contacting a zeolite with an aqueous solution of hydrochloric acid containing 4 to 8 gram-equivalents of HCl (4–8N HCl) at a temperature in the range of from about 70 to about 100° C., under about 1 to about 10 atm pressure, and for a period of from 1 to 20 hours to produce an aluminum-reduced zeolite; (2) contacting said aluminum-reduced zeolite with a metal compound under conditions sufficient to produce a metal-promoted zeolite; and (3) calcining said metal-promoted zeolite at 450° C. to 650° C. for 3 to 15 hours wherein the metal of said metal compound is selected from the group consisting of gallium, platinum, and combinations thereof.

32. A process according to claim 31 wherein said process for converting is carried out in the presence of hydrogen.

33. A process according to claim 28 wherein said metal is gallium.

34. A process according to claim 28 wherein said metal is platinum.

35. A process according to claim 17 wherein said zeolite is ZSM-5.

36. A process according to claim 33 wherein said zeolite is ZSM-5.

37. A process according to claim 34 wherein said zeolite is ZSM-5.

* * * * *